United States Patent [19]
Robertelli

[11] 3,987,549
[45] Oct. 26, 1976

[54] DENTAL PROPHYLACTIC HANDPIECE

[75] Inventor: Paul Robertelli, Manhasset, N.Y.

[73] Assignee: Lawrence Peska Associates, Inc., New York, N.Y. ; a part interest

[22] Filed: Oct. 6, 1975

[21] Appl. No.: 620,210

[52] U.S. Cl. ................................................ 32/59
[51] Int. Cl.² ........................................... A61C 3/06
[58] Field of Search .................. 279/102, 1 Q, 1 SG; 408/227; 32/58, 59

[56] References Cited
UNITED STATES PATENTS

| | | |
|---|---|---|
| 2,403,136 | 7/1946 | Stoner .................................. 279/1 Q |
| 2,965,383 | 12/1960 | Steiner et al ........................ 279/102 |

*Primary Examiner*—Robert Peshock
*Attorney, Agent, or Firm*—Joel Halpern

[57] ABSTRACT

A dental prophylactic handpiece is provided with a drivable tool-receiving member having a square opening which is internally serrated. The tool-receiving member, at least in the region of the opening, is resilient so as to permit variation in the size of the opening. A dental tool is detachably connected in said tool-receiving member by means of an enlarged shank having a complementary externally contoured surface including peripherally extending serrations.

6 Claims, 7 Drawing Figures

U.S. Patent    Oct. 26, 1976    3,987,549
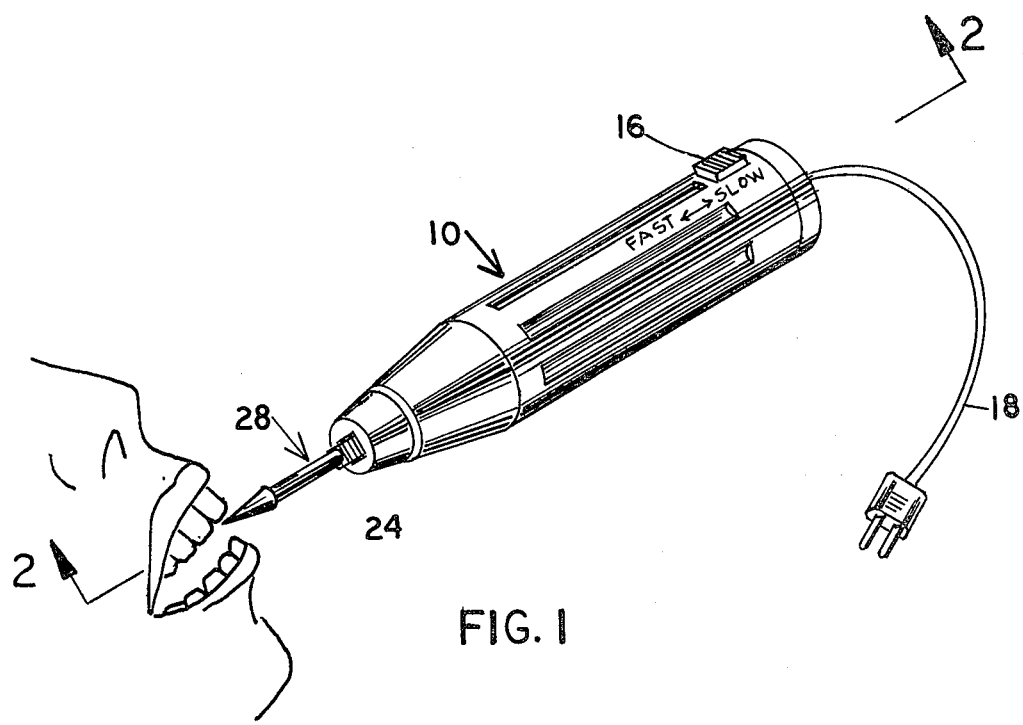
FIG. 1
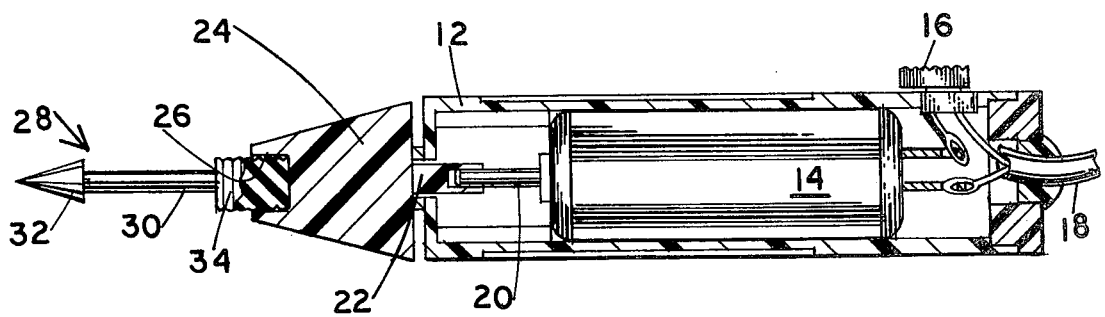
FIG. 2
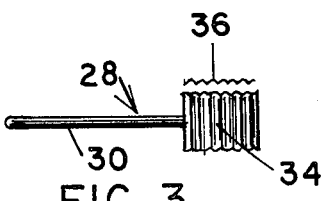
FIG. 3
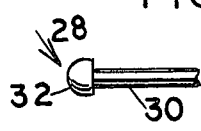
FIG. 4
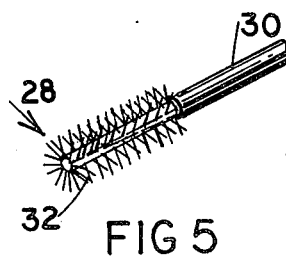
FIG 5
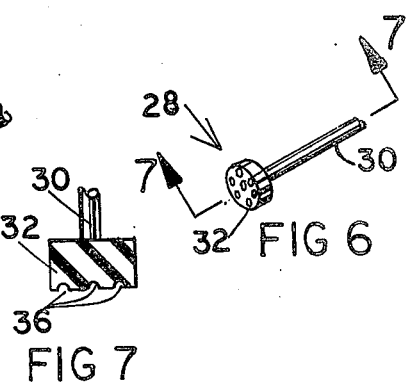
FIG 6
FIG 7

DENTAL PROPHYLACTIC HANDPIECE

BACKGROUND OF THE INVENTION

The present invention relates to dental prophylactic handpieces and more particularly to a handpiece of the character accommodating a detachable tool.

Dental prophylactic handpieces have been known heretofore. However such handpieces have required gearing or pulley arrangements in order to deliver the desired rotational force to an offset working tip. Such appliances are complicated and relatively expensive. The chucks of such handpieces have also been relatively complex, frequently requiring movable jaw components, which lead to increased cost.

SUMMARY OF THE INVENTION

It is one object of this invention to provide a dental prophylactic handpiece which permits the simple and secure detachable connection of a working tool.

It is another object of this invention to provide a dental prophylactic handpiece in which a tool can be detachably connected simply and in direct coaxial relation to the motor means of the device.

Still another object of this invention is the provision of a dental prophylactic handpiece in which a tool can be simply and securely detachably connected by cooperable tool shank and tool-receiving means of improved design.

Other objects and advantages of the invention will become readily apparent from the following description of the invention.

In accordance with the present invention there is provided a dental prophylactic handpiece comprising in combination:
- a hollow elongated housing having motor means mounted therein;
- a tool-receiving member mounted rotatably at one end thereof on said housing drivably connected to said motor means;
- a non-circular blind opening in the other end of said tool-receiving member, said tool-receiving member at least in the region thereof surrounding said opening being resilient and the inner surface of said opening being provided with circumferential serrations;
- and a dental tool detachably secured in said opening comprising a shank, a working tip integral with said shank located at one end thereof and an enlarged portion at the other end of said shank having an external surface of complementary configuration with the opening in said tool-receiving member including peripherally extending serrations thereon, the cross-sectional dimensions of said enlarged portion of the shank being greater than that of the corresponding dimensions of said opening, whereby insertion of said enlarged portion of said shank in said opening with the configurations of the opening and enlarged portion of the shank in aligned relation stresses said region of the tool-receiving member and effectuates a secure gripping of said dental tool therein.

BRIEF DESCRIPTION OF THE DRAWINGS

In order that the invention may be more fully understood it will now be described, by way of example, with reference to the accompanying drawings in which:

FIG. 1 is a perspective view of the dental prophylactic handpiece embodying the invention showing its application in use;

FIG. 2 is a side view, with the cover removed from the body of the device, of the handpiece shown in FIG. 1;

FIG. 3 shows the shank of a tool with its enlarged end adapted for connection in the body of the handpiece;

FIG. 4 shows one form of working tip which can be made integral with the shank of the tool;

FIG. 5 and FIG. 6 are perspective views of two additional forms of working tips which can be made integral with the shank of the tool; and FIG. 7 is a cross-sectional view of the working tip shown in FIG. 6 taken along section line 7—7 thereof.

DETAILED DESCRIPTION OF THE INVENTION

Referring to FIGS. 1 and 2 of the drawings there is shown a dental prophylactic handpiece 10 including a hollow elongated housing 12 within which there is mounted motor means 14. The housing may be made of metal; however, more desirably it is molded of a synthetic plastic material. The motor is preferably a low-inertia high speed D.C. electric motor capable of rotation at a speed up to approximately 10,000 revolutions per minute. It will be understood, of course, that the type of motor employed is not critical and may even be of the type in which a rotor is positioned within the housing of the device and is rotated by air pressure communicated to the rotor from an external source. The particular type of motor to be used can be appropriately selected depending upon the range of operational speeds to be used which, in turn, is dependent upon the type of prophylaxis treatment to be imparted, i.e. cleaning, polishing or cutting.

A two-way switch 16 may be located on the external surface of the housing for easy control of the motor. As is well known in the art, a variable resistor may be incorporated in the motor control circuit (not shown) in order to provide the desired motor speed control. A power cord 18 connects the motor to an external source of electrical supply.

The motor drive shaft 20 extends forwardly within the housing and is connected in known manner with shaft 22 of a tool-receiving member 24 which is mounted rotatably at the forward end of the housing. The shaft 22 may be supported in low-friction nylon bearings in a conventional manner.

As shown the tool-receiving member 24 is conically shaped. As will be described later this configuration not only contributes aesthetically to the appearance of the appliance; it may also serve a useful function in connection with the connection and release of the dental tools to be detachably connected. It will be observed that the shaft 22 of the tool-receiving member and the drive shaft of the motor are coaxially aligned so as to avoid the need for a bevel gear or pulley arrangement customarily employed with dental tools having an offset working head.

The tool-receiving member 24 is provided in its front end face with a non-circular opening 26 and the internal surface of such opening is given a plurality of peripheral serrations. Preferably the cross-sectional configuration of the opening 26 is square. The region of member 24 surrounding the opening is desirably made of a resilient material characterized by having a memory such that any distortion of the member due to the imposition of an externally applied force will be removed upon the removal of the external force. The entire member 24 may be made of such material where so desired. By giving the member the shape of a cone a lever effect is created by applying force to the base of the cone. This results in an enlargement of the opening 26 for a purpose to be explained.

A dental tool 28 is detachably connected in member 24 for rotation therewith. The tool comprises a shank 30 having a working tip integral therewith located at one end thereof. The other end of the shank is given an enlarged non-circular portion 34 having an external surface which is configured to complement the internal surface of opening 26 in the tool-receiving member 24. Peripherally extending serrations 36 are formed on the external surface of enlarged portion 34. The cross-sectional dimensions of the enlarged portion 34 are greater than the corresponding dimensions of opening 26. By inserting the tool with its enlarged portion 34 into opening 26 of member 24 the jaws of the opening are urged apart and the tool is securely clamped within the opening. In this step the member 24 may be grasped by the user of the device such that the application of an external force at the base of the conically shaped member tends to assist, through the aforesaid lever action, in separation of the jaws of the opening. Once the enlarged portion 34 of the tool is within opening 26 pressure at the base of the cone is released and by virtue of the memory of the material the jaws return to their initial unstressed condition and result in tight engagement of the internal surfaces of opening 26 with the external surfaces of the enlarged portion of the shank of the tool. The peripherally extending serrations of the enlarged portion of the shank and on the internal surface of the opening 26 serve to mechanically interlock and thereby prevent axial removal of the tool from member 24. The non-circular complementary configurations of enlarged portion 34 and opening 26 serve to insure positive locking of the tool and member during rotation. It has been found that the provision of a square configuration for both enlarged portion 34 and opening 26 results in an eminently satisfactory coupling of the components.

In FIG. 4 there is shown a button-shaped working tip and in FIG. 5 there is depicted a working tip in the form of a cylinder of relatively soft bristles.

The construction of the working tip shown in FIGS. 6 and 7 is of particular value in the cleaning of teeth with a powder or other cleansing material which can be contained within a plurality of blind bores 36 formed in the outer face of the disc-shaped tip. The working tips are preferably made of rubber.

From the foregoing it will be seen that a dental prophylactic handpiece has been provided which is easily manipulatable, possesses a minimum of operational components and affords improved means for attaching and removing selected dental tools to be employed in the cleaning or polishing of teeth. The removal of plaque from teeth is also greatly facilitated.

I claim:
1. A dental prophylactic handpiece comprising in combination:
   a hollow elongated housing having motor means mounted therein;
   a tool-receiving member mounted rotatably at one end thereof on said housing drivably connected to said motor means;
   a non-circular blind opening in the other end of said tool-receiving member, said tool-receiving member at least in the region thereof surrounding said opening being resilient and the inner surface of said opening being provided with circumferential serrations;
   and a dental tool detachably secured in said opening comprising a shank, a working tip integral with said shank located at one end thereof and an enlarged portion at the other end of said shank having an external surface of complementary configuration with the opening in said tool-receiving member including peripherally extending serrations thereon, the cross-sectional dimensions of said enlarged portion of the shank being greater than that of the corresponding dimensions of said opening, whereby insertion of said enlarged portion of said shank in said opening with the configurations of the opening and enlarged portion of the shank in aligned relation stresses said region of the tool-receiving member and effectuates a secure gripping of said dental tool therein.

2. A dental prophylactic handpiece according to claim 1, wherein said opening and said enlarged portion of said shank are given a square configuration.

3. A dental prophylactic handpiece according to claim 1, wherein the said working tip of said dental tool is an integral, flexible disc having a plurality of axially extending blind bores in the outer face thereof.

4. A dental prophylactic handpiece according to claim 1, wherein the said working tip of said dental tool is an integral flexible conical element.

5. A dental prophylactic handpiece according to claim 1, wherein the axis of said shank is coaxial with the drive shaft of said motor means.

6. A dental prophylactic handpiece according to claim 1, wherein said tool-receiving member is formed with a conical configuration.

* * * * *